United States Patent
Funamura et al.

(10) Patent No.: US 7,806,874 B2
(45) Date of Patent: Oct. 5, 2010

(54) LIQUID COINJECTOR

(75) Inventors: Shigeaki Funamura, Fukuroi (JP); Ichiro Kitani, Fukuroi (JP); Katsuki Nagata, Fukuroi (JP)

(73) Assignee: Tyco Healthcare Group LP, Mansfield, MA (US)

( * ) Notice: Subject to any disclaimer, the term of this patent is extended or adjusted under 35 U.S.C. 154(b) by 289 days.

(21) Appl. No.: 11/747,641

(22) Filed: May 11, 2007

(65) Prior Publication Data
US 2007/0265581 A1 Nov. 15, 2007

(30) Foreign Application Priority Data
May 15, 2006 (JP) .............................. 2006-134658

(51) Int. Cl.
*A61M 5/00* (2006.01)
(52) U.S. Cl. .................................................... 604/246
(58) Field of Classification Search .................. 604/246
See application file for complete search history.

(56) References Cited

U.S. PATENT DOCUMENTS

| 2,335,085 | A | * | 11/1943 | Arthur .................... 137/625.11 |
| 2,971,522 | A | * | 2/1961 | Lewis ......................... 137/101 |
| 3,674,235 | A | * | 7/1972 | Porter et al. ................. 251/162 |
| 3,957,082 | A |   | 5/1976 | Fuson et al. |
| 4,082,095 | A |   | 4/1978 | Mendelson et al. |
| 4,146,055 | A | * | 3/1979 | Ryder et al. ............ 137/625.41 |
| 4,832,083 | A | * | 5/1989 | Bruner ........................ 137/861 |
| 5,135,026 | A | * | 8/1992 | Manska ....................... 137/555 |
| 5,256,160 | A |   | 10/1993 | Clement |
| 5,261,459 | A |   | 11/1993 | Atkinson et al. |
| 5,328,478 | A |   | 7/1994 | McVay |
| 5,540,668 | A | * | 7/1996 | Wilson et al. ................ 604/248 |
| 6,461,335 | B1 |   | 10/2002 | Noecker |
| 7,131,625 | B2 | * | 11/2006 | Wieder ........................ 249/103 |
| 7,232,428 | B1 | * | 6/2007 | Inukai et al. ................. 604/248 |
| 7,458,112 | B1 | * | 12/2008 | Yang ............................. 4/601 |
| 2002/0017328 | A1 | * | 2/2002 | Loo ....................... 137/625.47 |
| 2007/0068587 | A1 | * | 3/2007 | Utterberg et al. ............. 137/872 |
| 2007/0221275 | A1 | * | 9/2007 | Amley et al. ................. 137/512 |
| 2008/0086093 | A1 | * | 4/2008 | Steppe et al. ................ 604/246 |
| 2008/0294148 | A1 | * | 11/2008 | Gardner .................... 604/891.1 |

FOREIGN PATENT DOCUMENTS

DE 19819432 A1 11/1999
JP S62-172962 7/1987

\* cited by examiner

*Primary Examiner*—Nicholas D Lucchesi
*Assistant Examiner*—Diva Ranade
(74) *Attorney, Agent, or Firm*—Lawrence A. Chaletsky, Esq.

(57) ABSTRACT

A liquid coinjector is provided in which one or more connection ports may be connected to an outlet port and in which a valve body is provided for selecting the connection arrangement, the valve body being movable in an axial direction within a chamber of a main body.

7 Claims, 6 Drawing Sheets

LIQUID COINJECTOR

CROSS-REFERENCE TO RELATED APPLICATION

The present application claims priority to related Japanese Patent Application No. 2006-134658, filed May 15, 2006, the entirety of which is herein incorporate by reference.

FIELD OF THE INVENTION

The present invention generally relates to a liquid coinjector.

BACKGROUND OF THE INVENTION

Supply of a predetermined physiological salt solution or liquid medicine or the like to the body of a patient is conventionally administered employing a plurality of transfusion tubes, the operation performed in such cases being based on communication and cutoff of these transfusion tubes employing a liquid coinjector. These liquid coinjectors comprise three branch tubes. The liquid coinjector is configured to comprise a chamber that communicates with the three branch tubes and a valve body that rotates within the chamber as a result of the operation of an operating part, communication and cutoff between desired branch tubes being made possible by operation of the operating part to rotate the valve body.

However, in the liquid coinjector described above, the operating part protrudes from the circumferential surface of the chamber and, as a result, the tube members and so on connected to the branch tube sometimes become entwined on the operating part or come into contact with the body of the patient causing the operating part to rotate. For this reason, a liquid coinjector with a cylindrically-formed chamber in which, by movement of the operating part in the direction around the axis of the chamber to afford communication and cutoff between a predetermined branch tube and chamber, the flow passage of a branch tube can be switched without need for the operating part to protrude from the circumferential surface of the chamber has been developed (for example, see Japanese Laid-open Patent Application No. S62-172962). This liquid coinjector is configured by provision of two branch tubes about the circumferential surface of a substantially cylinder-shaped chamber, the two branch tubes being able to be opened and closed by rotation of the valve body in the direction around the axis of the chamber.

However, this liquid coinjector comprises only two branch tubes, and communication and cutoff of these two branch tubes alone is performed. Accordingly, this liquid coinjector cannot be used to link a plurality of transfusion tubes and so on as employed in medical treatments and facilitate communication and cutoff between these transfusion tubes. An additional problem inherent to this liquid coinjector pertains to the rotational operation of the valve body to afford communication and cutoff between the two branch tubes which is difficult to implement.

With the foregoing conditions in mind, it is an object of the present invention to provide an improved liquid coinjector.

SUMMARY OF THE INVENTION

In one aspect of the present invention, a liquid coinjector generally comprises a main body defining a chamber having an axis. First and second connection ports extend outwardly from the chamber and a third connection port extends outwardly from the chamber at a predetermined angle with respect to the first and second connection ports. A valve body is arranged in the chamber and is movable within the chamber in a direction parallel to the axis between a first position in which both the second and third connection ports are in fluid flow communication with the first connection port and a second position in which only the third connection port is in fluid flow connection with the first connection port. The coinjector is characterized by the valve body defining a first groove part and a second groove part. The first groove part is shaped so as to provide the fluid flow communication between the first connection port and the second and third communication ports when the valve body is in the first position. The second groove part is shaped so as to provide the fluid flow communication between the first connection port and the third communication port when the valve body is in the second position. The valve body includes an isolating surface region by fluid flow connection from the second connection port is cut off when the valve body is in the second position.

Other features will be in part apparent and in part pointed out hereinafter.

BRIEF DESCRIPTION OF THE DRAWINGS

Corresponding reference characters indicate corresponding parts throughout the drawings.

DETAILED DESCRIPTION OF THE PREFERRED EMBODIMENTS

Figure 1:
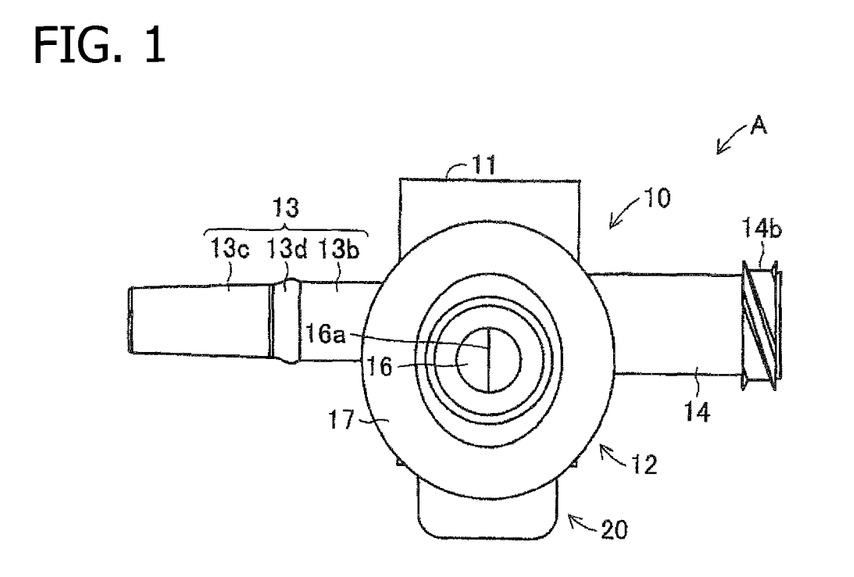
FIG. 1 is a plan view of a liquid coinjector pertaining to one embodiment of the present invention.
Figure 2:
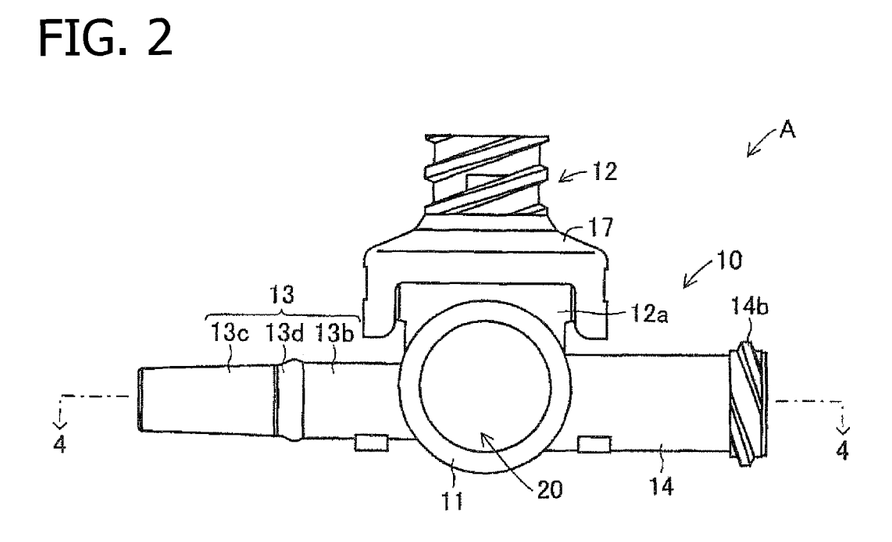
FIG. 2 is a side view of the liquid coinjector.
Figure 3:
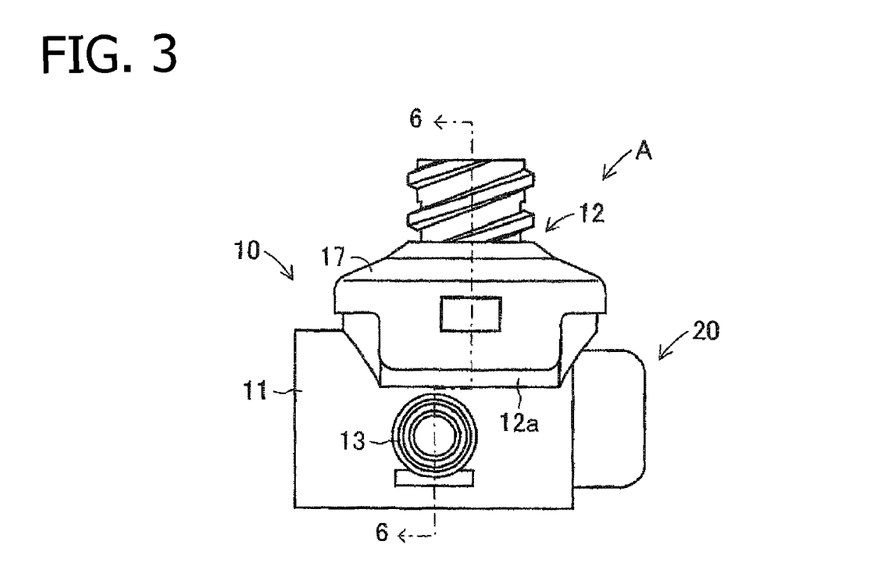
FIG. 3 is a front view of the liquid coinjector.

The liquid coinjector pertaining to the present invention will be hereinafter described in detail with reference to the drawings. FIGS. 1 to 3 show a liquid coinjector A pertaining to one embodiment of the present invention, the liquid coinjector A comprising a liquid coinjector main body 10, a cover 17 and a valve body 20. The liquid coinjector main body 10 is configured from a cylinder-shaped chamber 11 of which the axial direction is arranged in the horizontal, a confluent branch part 12 formed in the upper part on the outer circumferential surface of the chamber 11, and a downstream branch tube 13 and upstream branch tube 14 serving as a pair of main branch tubes of the present invention that link with and extend in the horizontal direction along the same axis from the front and rear sides (left and right sides in FIG. 1 and FIG. 2) of the outer circumferential surface of the chamber 11.

Figure 4:
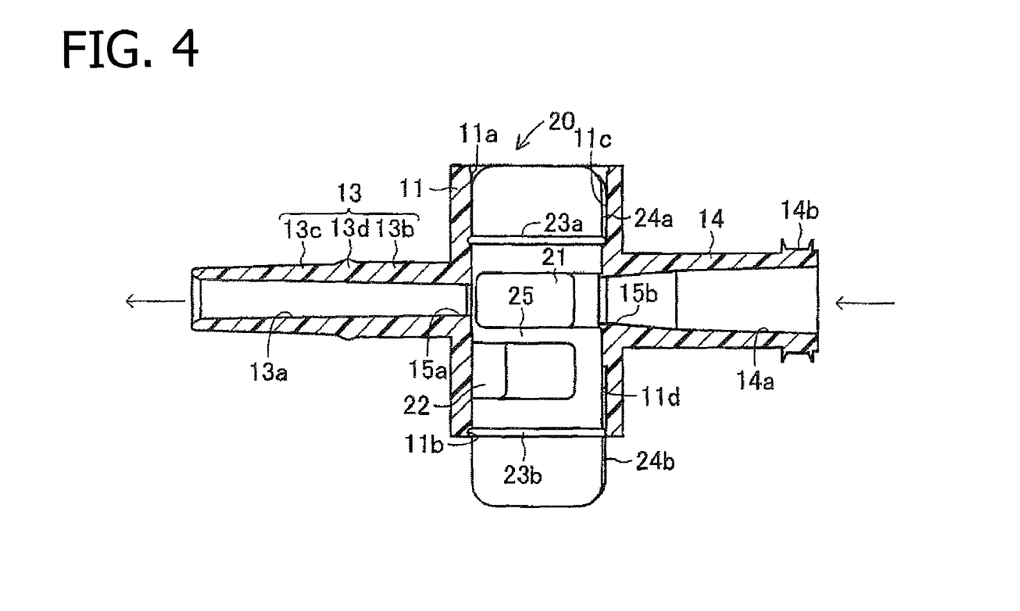
FIG. 4 is a cross-sectional view along the line 4-4 of FIG. 2.
Figure 5:
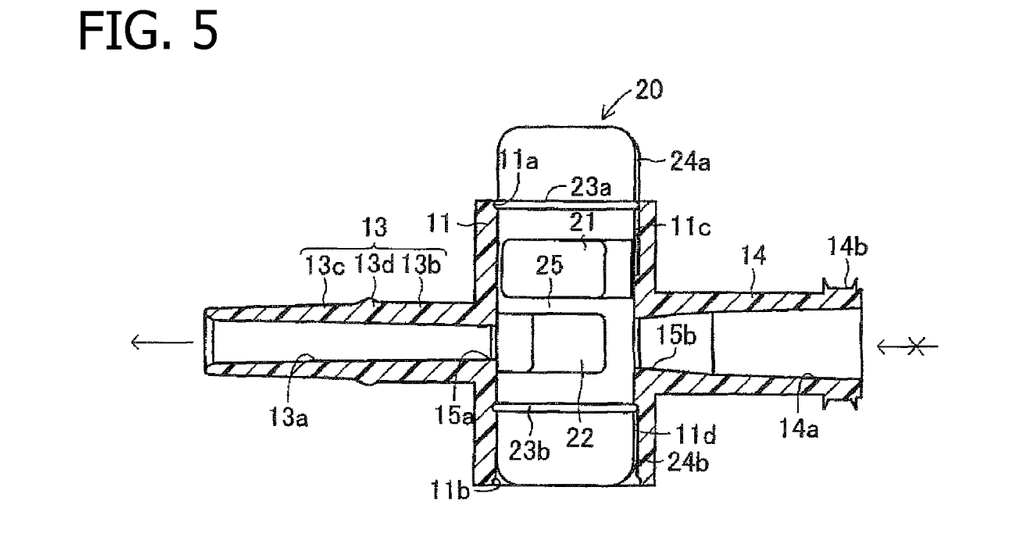
FIG. 5 is a transverse cross-sectional view of the liquid coinjector in a state in which the valve body has been moved from the state shown in FIG. 4.

That is to say, the confluent branch part 12, downstream branch tube 13 and upstream branch tube 14 are provided with an interval in the circumferential direction in the same position along the axial direction of the outer circumferential surface of the chamber 11, the confluent branch part 12 extending upward and orthogonal with the downstream branch tube 13 and the upstream branch tube 14 that extend in the horizontal direction. The chamber 11 has a substantially uniform diameter and is formed in a substantially cylinder shape extending in the axial direction as shown in FIG. 4 and FIG. 5, engage recesses 11a, 11b serving as engage parts of the present invention being formed along the inner circumference in each of one end-side section and another end-side section in the left-right directions (up-down direction in FIG. 4 and FIG. 5) of the inner circumferential surface thereof. In addition, guide grooves 11c, 11d serving as guide parts of the present invention are formed extending in the axial direction in rear (right-side section of FIG. 4 and FIG. 5) left and right-side sections of the inner circumferential surface of the chamber 11.

Furthermore, two communication holes 15a, 15b are formed in sections opposing the centre section in the axial direction of the chamber 11. The downstream branch tube 13 is provided in a section of the outer circumferential surface of the chamber 11 opposing the communication hole 15a, a flow passage 13a formed in the interior of the downstream branch tube 13 communicating with the interior of the chamber 11 by way of the communication hole 15a. In addition, the upstream branch tube 14 is provided in a section of the outer circumferential surface of the chamber 11 opposing the communication hole 15b, a flow passage 14a formed in the interior of the upstream branch tube 14 communicating with the interior of the chamber 11 by way of the communication hole 15b.

Figure 6:
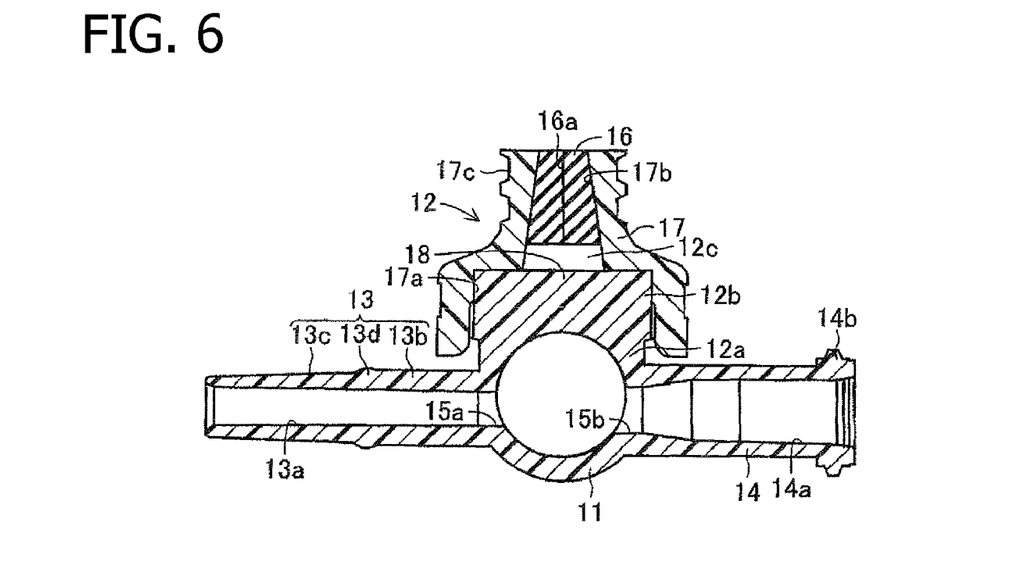
FIG. 6 is a vertical cross-sectional view of the liquid coinjector.

As shown in FIG. 6, the confluent branch part 12 formed above the chamber 11 is configured from a confluent branch tube main body 12a integrally configured with the chamber 11, a cover 17 affixed to an upper-end opening part of the confluent branch tube main body 12a, and a rubber stopper 16 affixed to an upper-side section of the interior of the cover 17. The confluent branch tube main body 12a is formed in a cylinder shape with a shorter length in the axial direction and a larger diameter than the downstream branch tube 13 and upstream branch tube 14. In addition, FIG. 6 shows a cross section along the line 6-6 of FIG. 3, the left and right of the confluent branch tube main body 12a being separated by provision of a barrier 18. Accordingly, the left-right sections of the confluent branch tube main body 12a shown in FIG. 3 define space parts provided about the barrier 18.

In addition, a large diameter part 12b formed with a slightly larger diameter than the confluent branch tube main body 12a is provided in the upper part on the outer circumferential surface thereof, and the cover 17 is affixed to the large diameter part 12b. The cover 17 is formed in a substantially cap shape with an open upper-face opening part, an engage recess 17a engageable with the large diameter part 12b of the confluent branch tube main body 12a being formed in the lower part on the inner circumferential surface thereof. The cover 17 is affixed to the confluent branch tube main body 12a by engagement of the cover 17 with the large diameter part 12b. In addition, a taper in which the diameter of the upper-end opening side narrows from the diameter of the lower side is provided in an inner circumferential surface 17b of the upper-side section of the cover 17. The rubber stopper 16 is affixed to the upper part of the inner circumferential surface 17b of the cover 17. In addition, a screw part 17c for linking connectors and so on is formed in the outer circumferential surface of the upper-side section of the cover 17.

In addition, the rubber stopper 16 configured from natural rubber or synthetic rubber is inserted in the upper part-side section of the inner circumferential surface 17b of the interior of the cover 17 in which the taper is provided to cover the interior upper-end side section of the cover 17. In addition, a slit 16a that passes vertically between the interior side of the chamber 11 and the exterior side of the confluent branch part 12 is provided in the rubber stopper 16 to form a flow passage of the confluent branch tube 12. When the confluent branch part 12 is not being used, a state in which this slit 16a is closed due to the elasticity of the rubber stopper 16 is established. The slit 16a and a space part 12c from which the flow passage of the confluent branch part 12 is configured are formed below the rubber stopper 16 in the interior of the cover 17.

The downstream branch tube 13 is integrally formed with the chamber 11 and configured from a base-end part 13b positioned toward the chamber 11 side and a male luer part 13c narrower than the base-end part 13b positioned toward the tip-end side. In addition, the male luer part 13c is formed in a shape that narrows to the tip end, the tip-end side thereof being narrower than the base-end part 13b side. A protruding part 13d is formed around the circumference in a boundary part between the base-end part 13b and male luer part 13c on the outer circumferential surface of the downstream branch tube 13.

In addition, the upstream branch tube 14 is integrally formed with the chamber 11, a flow passage 14a comprising a tapered hole part being formed in its interior. The flow passage 14a communicates with a communication hole 15b and is formed in a tapered shape with reducing diameter of the communication hole 15b side section toward the communication hole 15b and with increasing diameter away from the communication hole 15b. In addition, the upstream-side section (right-side section of FIG. 4 to FIG. 6) of the flow passage 14a is configured in a tapered shape with gradually increasing diameter toward an opening part of the upstream branch tube 14. A linking screw part 14b is formed in the outer circumferential surface of the opening part of the upstream branch tube 14.

Figure 7:
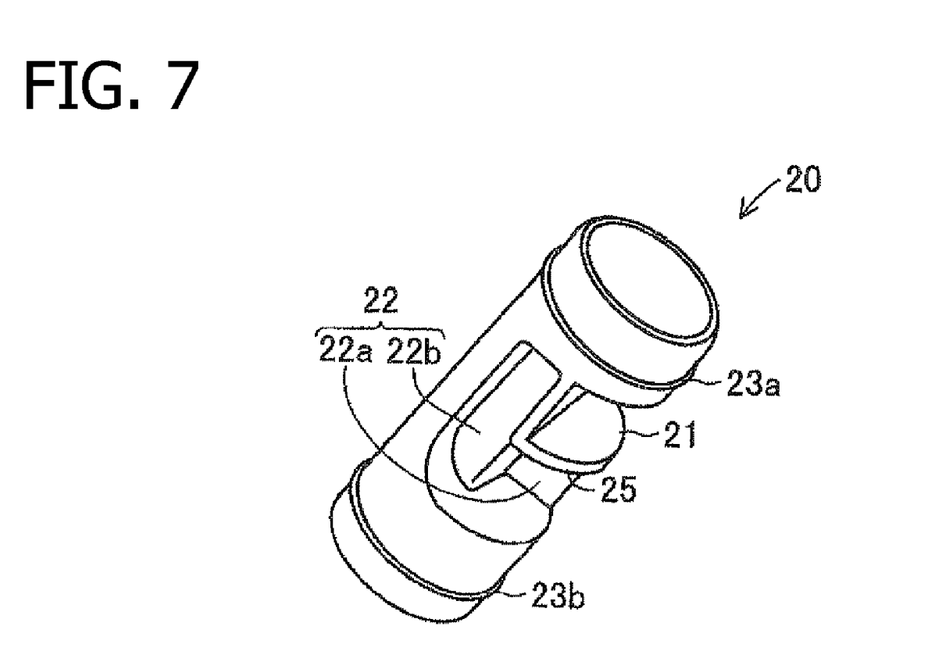
FIG. 7 is a perspective view of a valve body.
Figure 8:
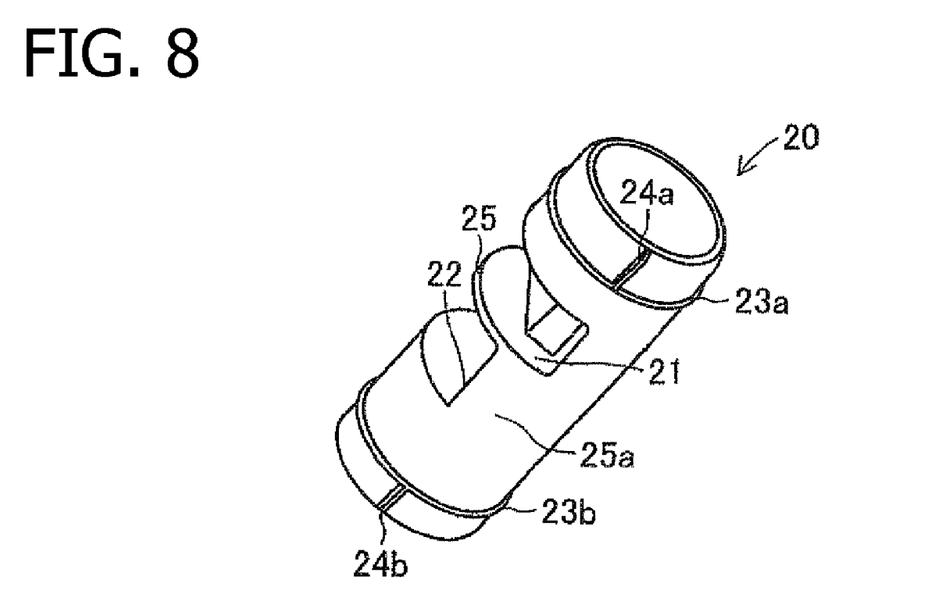
FIG. 8 is a perspective view of the state of the valve body of FIG. 7 from another direction.
Figure 9:
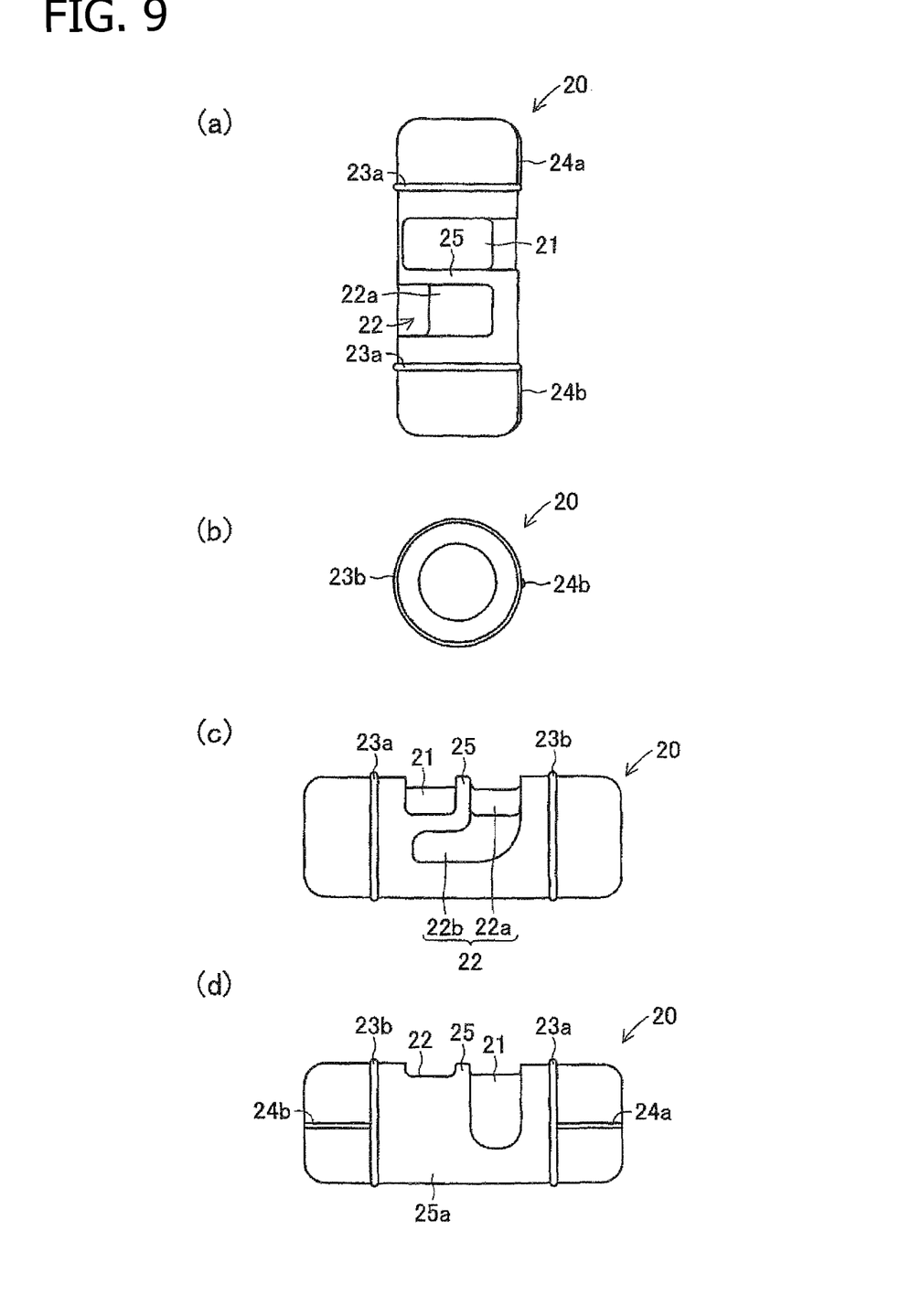
FIG. 9 shows the valve body, (a) is a plan view, (b) is a front view, (c) is a left-side view, and (d) is a right-side view.

The valve body 20 is arranged in the chamber 11 to be movable in the axial direction within the chamber 11 as a result of its end part being pushed into the interior side of the chamber 11. In addition, as shown in FIG. 7 to FIG. 9, the valve body 20 is formed in a substantially cylinder shape, and a first groove part 21 and second groove part 22 are formed in the outer circumferential surface thereof. The first groove part 21 is configured from a substantially I-shaped notch groove that extends substantially half the circumference along a section in the outer circumferential surface of the valve body 20 slightly to a first end-part side from the centre in the axial direction.

In addition, the second groove part 22 is configured as a substantially L-shaped notch groove comprising a circumferential direction groove part 22a that extends along the outer circumferential surface of the valve body 20 in parallel with the first groove part 22 along a section in the outer circumferential surface of the valve body 20 slightly toward the other end-part side from the centre in the axial direction, and an axial direction groove part 22b that extends toward the first end-part side in the axial direction bending from a first end part of the circumferential direction groove part 22a. The axial direction groove part 22b of the second groove part 22 is provided in a position with a predetermined interval to the first end part of the first groove part 21, and the other end part of the circumferential direction groove part 22a of the second groove part 22 is positioned in the forward side (one end side of the first groove part 21) along the circumferential direction from the other end part of the first groove part 21.

The length of both the first groove part 21 and the second groove part 22 in the circumferential direction of the valve body 20 is set equal to substantially half the circumference, and the interval between the first groove part 21 and the circumferential direction groove part 22a of the groove part 22 is set substantially equal to the interval between the first groove part 21 and the axial direction groove part 22b of the second groove part 22. That is to say, the other end part of the circumferential direction groove part 22a of the second groove part 22 extends to the front side along the circumferential direction from the other end part of the first groove part 21 only the amount that the axial direction groove part 22b of the second groove part 22 protrudes in the circumferential direction from the first end part of the first groove part 21. In addition, an equal interval is maintained between the first groove part 21 and the second groove part 22 along their entirety. A weir part 25 is formed along the outer circumferential surface of the valve body 20 between the first groove part 21 and the circumferential direction groove part 22a of the second groove part 22.

In addition, the length in the axial direction of the valve body 20 is set larger than the length in the axial direction of the chamber 11, the valve body 20 being configured so that, when arranged in the chamber 11, the end part of the valve body 20 protrudes from the chamber 11. Engage protrusions 23a, 23b are formed along the circumference of the valve body 20 in a section of the outer circumferential surface positioned a length amount toward the centre side from the two end parts along the axial direction thereof that is slightly longer than the difference in length between the valve body 20 and the chamber 11. The engaged parts of the present invention are configured from these engage protrusions 23a, 23b and are detachably engageable with the engage recesses 11a, 11b of the chamber 11.

Furthermore, guide protrusions 24a, 24b serving as the guide parts of the present invention with which guide grooves 11c, 11d of the chamber 11 are respectively engageable are formed in the outer circumferential surface of the valve body 20 in end-part side sections from the engage protrusions 23a, 23b. For this reason, the valve body 20 is only movable in the axial direction in the chamber 11 in a state in which the guide protrusions 24a, 24b are engaged with the guide grooves 11c, 11d and rotation in the direction about the axis thereof is stopped.

In addition, as shown in FIG. 4, the engage protrusion 23b and engage recess 11b are engaged when the valve body 20 is positioned in a first side in the left to right direction (when positioned in the lower side in FIG. 4 in a state in which the upstream branch tube 14 and chamber 11, and downstream branch tube 13 and chamber 11 are in communication as shown by the arrow) and, as shown in FIG. 5, the engage protrusion 23a and engage recess 11a are engaged when the valve body 20 is positioned in the other side in the left to right direction in FIG. 3 (when positioned in the upper side in FIG. 5 in a state in which the upstream branch tube 14 is closed by the valve body 20 and the chamber 11 and downstream branch tube 13 are in communication as shown by the arrow).

In this case, the engagement between the engage protrusion 23a and engage recess 11a and the engagement between the engage protrusion 23b and engage recess 11b is unstable, and the tip end of the valve body 20 is pushed inside the chamber 11 by an operator, whereby the valve body 20 is moved in the direction of pushing. When the engage protrusion 23a and engage recess 11a or the engage protrusion 23b and engage recess 11b are engaged, the valve body 20 remains fixed in the position shown in FIG. 4 and FIG. 5 provided it is not subject to a force greater than the operating force of the operator.

In addition, the valve body 20 arranged in the chamber 11 exists in a state in which the face shown in FIG. 9(a) points upward, the face shown in FIG. 9(c) points toward the downstream branch tube 13 side, and the face shown in FIG. 9(d) points toward the upstream branch tube 14 side. For this reason, as shown in FIG. 4, when the valve body 20 is positioned in either the left or the right direction, the lower-end part of the first groove part 21 opposes the communication hole 15b in the state shown in FIG. 9(d), and the chamber 11 and upstream branch tube 14 communicate by way of the first groove part 21. In addition, the left-side end part of the axial direction groove part 22b of the second groove part 22 opposes the communication hole 15a in the state shown in FIG. 9(c), and the chamber 11 and downstream branch tube 13 communicate by way of the second groove part 22.

In this case, the barrier 18 is positioned above the weir part 25, and the upper face of the weir part 25 and lower face of the barrier 18 contact in a substantially close fitting state. In addition, because the space part 12c of the confluent branch part 12 is positioned above the barrier 18, the first groove part 21 and second groove part 22 communicate by way of the space part 12c. Accordingly, in this state, liquid medicine or the like can flow from the upstream branch tube 14 to the downstream branch tube 13 by way of the chamber 11 and confluent branch part 12. In this case, the liquid medicine or the like that flows from the upstream branch tube 14 into the first groove part 21 flows over the barrier 18 into the second groove part 22. For this reason, the liquid medicine or the like passes through the space part 12c above the chamber 11, and stagnation of air and so on in the chamber 11 and space part 12c can be prevented.

In addition, as shown in FIG. 5, when the valve body 20 is positioned in the other left or right direction, a left-side outer circumferential surface part 25a of the first groove part 21 closes the communication hole 15b in the state shown in FIG. 9(d) resulting in cutoff of the chamber 11 from the upstream branch tube 14. The outer circumferential surface part 25a constitutes the cutoff surface of the present invention. In addition, a state in which the right-side end part of the axial direction groove part 22b of the second groove part 22 shown in FIG. 9(c) opposes the communication hole 15a and the downstream branch tube 13 communicates with the chamber 11 by way of the second groove part 22 is maintained. That is to say, while a state of communication between the communication hole 15a and the axial direction groove part 22b is maintained when the valve body 20 is moved to the left and the right in the chamber 11, the communication hole 15b communicates with the first groove part 21 and is cut off by the outer circumferential surface part 25a.

Figure 10:
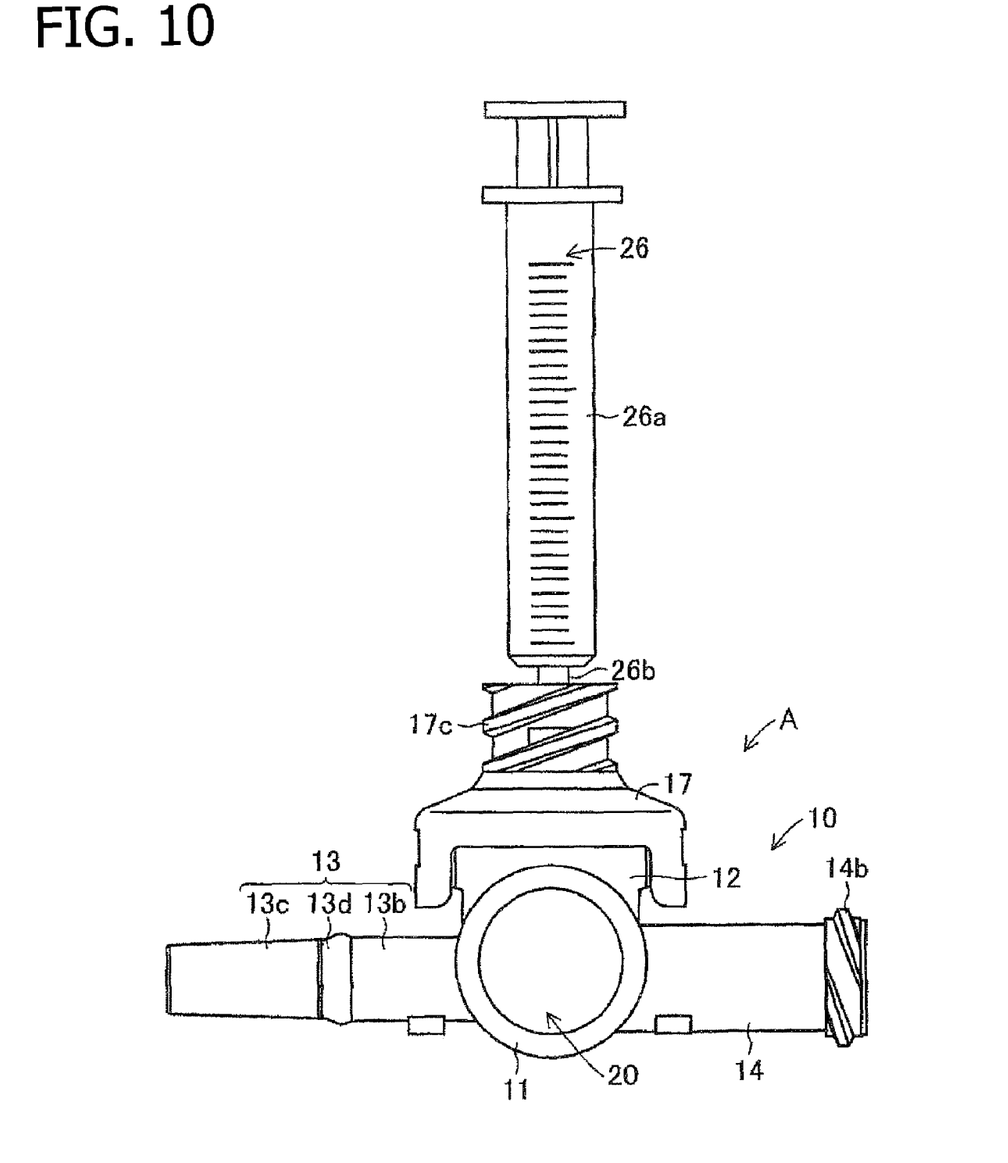
FIG. 10 is a side view of the liquid coinjector to which a cylinder is affixed.

In addition, as shown in FIG. 10, a cylinder 26 can be detachably affixed to the confluent branch part 12. The cylinder 26 comprises a liquid medicine housing part 26a for housing the liquid medicine or the like, and a narrow cylinder-shaped male luer part 26b. The liquid medicine housing part 26a communicates with the space part 12c of the confluent branch part 12 as a result of pressing of the male luer part 26b into the slit 16a of the rubber stopper 16. A close-fitting state is established between the male luer part 26b and the inner circumference of the slit 16a at this time due to the elasticity of the rubber stopper 16.

For this reason, while the upstream branch tube 14 and downstream branch tube 13 are in communication as shown in FIG. 4 to afford flow of liquid medicine or the like from the upstream branch tube 14 side to the downstream branch tube 13 side, other liquid medicine or the like can be mixed from the cylinder 26 into this liquid medicine or the like. In addition, in a cutoff state between the chamber 11 and upstream branch tube 14 as shown in FIG. 5, one type of liquid medicine or the like can be caused to flow from the cylinder 26 to the downstream branch tube 13.

Using this configuration, when a predetermined liquid medicine is to be supplied into the body of a patient (not shown in the diagram), a rear-end part of a transfusion tube (not shown in the diagram) to which an indwelling needle that punctures and is retained in the patient is connected to the downstream side branch tube 13. In addition, a male luer part provided in the tip-end part of the transfusion tube that extends from a receptacle or the like for housing the liquid medicine to be supplied to the patient is connected to the upstream branch tube 14. Liquid medicine is supplied to the patient by operation of the valve body 20 and feeding liquid medicine from a receptacle or the like to the patient in the state in which the indwelling needle has punctured and is retained in the body of the patient. In addition, when another liquid medicine or the like in addition to the liquid medicine supplied from the receptacle or the like is to be supplied, the other liquid medicine or the like is injected from the confluent branch part 12 by way of the cylinder 26 into the chamber 11.

That is to say, when the valve body 20 is operated in a state in which the male luer part 26b of the cylinder 26 is inserted into the slit 16a of the rubber stopper 16 so that the communication hole 15b and first groove part 21 are in communication, each of the cylinder 26, downstream branch tube 13 and upstream branch tube 14 communicate by way of the chamber 11 and the space part 12c of the confluent branch part 12. Communication between the cylinder 26, downstream branch tube 13 and upstream branch tube 14 can be visually ascertained according to whether or not the cylinder 26 is affixed at this time and the position of the valve body 20.

In addition, when the valve body 20 is operated so that the communication hole 15b is cut off by the outer circumferential surface part 25a of the valve body 20, the cylinder 26 and downstream branch tube 13 communicate by way of the chamber 11 and space part 12c of the confluent branch part 12. In addition, prior to the indwelling needle being pierced in and retained in the body of the patient, a small amount of liquid medicine is discharged from the tip end of the retaining needle. As a result, the air within the flow passage of the chamber 11 or confluent branch part 12 or the like can be discharged with this liquid medicine to the exterior. In addition, the liquid coinjector A can be used in a state in which it is affixed to a plate-like affixing member or the like. In this case, a plurality of liquid coinjectors A are employed, and different liquid medicines or the like can be supplied to the body of the patient from each of the liquid coinjectors A.

In this way, in the liquid coinjector A pertaining to this embodiment, the upstream branch tube 14 can be cut off from the chamber 11 and the upstream branch tube 14 and downstream branch tube 13 can communicate by way of the space part 12c and so on of the confluent branch part 12 as a result of pushing of the end part of the valve body 20 protruding from the chamber 11 into the chamber 11 and reciprocal motion of the valve body 20 in the chamber 11. In addition, a slit 16a is provided in the rubber stopper 16 of the confluent branch part 12, and the cylinder 26 can communicate with the interior of the chamber 11 by inserting of a male luer member 26b of the cylinder 26 into the slit 16a.

Accordingly, by moving the valve body 20 in a state in which the male luer part 26b of the cylinder 26 is inserted in the slit 16a of the rubber stopper 16, each of the cylinder 26, downstream branch tube 13 and upstream branch tube 14 can communicate by way of the chamber 11 and the space part 12c of the confluent branch part 12. As a result, two types of liquid medicine or the like can be supplied to the body of a patient. In addition, communication between the downstream branch tube 13 and the upstream branch tube 14 alone is possible by detachment of cylinder 26 in this state to close the rubber stopper 16.

Furthermore, communication between the cylinder 26 and downstream branch tube 13 alone is possible by cutoff of the upstream branch tube 14 from the chamber 11 in the state in which the male luer part 26b of the cylinder 26 is inserted into the slit 16a of the rubber stopper 16. By virtue of this, a single type of liquid medicine or the like can be supplied to the body of the patient. Furthermore, by detaching the cylinder 26 in this state, the flow passages of each of the confluent branch part 12, downstream branch tube 13 and upstream branch tube 14 can be closed.

In addition, because the switching operation between communication and cutoff of the downstream branch tube 13 and the upstream branch tube 14 requires only that the end part of the valve body 20 be pushed into the interior of the chamber 11, the position of the valve body 20 can be visually ascertained very simply and easily, and operation errors are unlikely. In addition, because the need for special provision of an operating part or the like to move the valve body 20 is eliminated and the two end parts of the valve body 20 serve as the operating part, the obstruction created by the protrusion of the opening part and so on from the outer circumferential surface of the chamber 11 is removed. Furthermore, if the liquid coinjector A is positioned above the bed, because a state in which the axial direction of the chamber 11 lies along the horizontal direction is established, contact with the body of the patient resulting in a change in the position of the valve body 20 is unlikely to occur.

In addition, in the liquid coinjector A pertaining to the present invention, because a first groove part 21 and second groove part 22 are provided as two notched grooves in the outer circumferential surface of the valve body 20 and switching between flow passages can be carried out using an outer circumferential surface part 25a serving as a cutoff surface which constitutes one part of the outer circumferential surface, the valve body 20 can be formed as a simple structure that affords a reliable switching between the flow passages. Furthermore, by provision of guide grooves 11c, 11d that extend in the axial direction in the inner circumferential surface of the chamber 11 and guide protrusions 24a, 24b that engage with the guide grooves 11c, 11d in the valve body 20, the valve body 20 is able to be moved only in the axial direction with respect to the chamber 11.

Because, by virtue of this, rotation of the valve body 20 in the direction around the axis of the chamber 11 is prevented and, accordingly, the valve body 20 is moved along its proper trajectory, displacement of the position of the valve body 20 with respect to the chamber 11 resulting in imprecise switching of the flow passages does not occur. In addition, engage recesses 11a, 11b extending in the inner circumferential direction are provided in each of the two side-end sections of the inner circumferential surface of the chamber 11, and these engage protrusions 23a, 23b are detachable with respect to the engage recesses 11a, 11b provided in the valve body 20.

By engagement of the engage recess 11a with the engage protrusion 23a and the engage recess 11b with the engage protrusion 23b, the valve body 20 can be maintained stationary in a predetermined position of the chamber 11. Proper operation of the valve body 20 is possible as a result. Furthermore, because communication between the cylinder 26 and the chamber 11 is made possible by affixing of the rubber stopper 16 to the cover 17 affixed to the confluent branch tube main body 12a and passing of the male luer part 26b of the cylinder 26 through the slit 16a of the rubber stopper 16, the flow passage of the confluent branch part 12 is able to communicate with and be cut off from the chamber 11 based on a simple method.

In addition, the liquid coinjector pertaining to the present invention is not to be regarded as being restricted to the embodiment described above and may be modified as appropriate. For example, while in the embodiment described above the guide grooves 11c, 11d are provided in the chamber 11 and the guide protrusions 24a, 24b are provided in the valve body 20 to prevent rotation of the valve body 20 in the direction around the axis, replacing the guide grooves 11c, 11d and the guide protrusions 24a, 24b, rotation in the direction around the axis of the valve body can be prevented by formation of the shape of the outer circumferential surface of the valve body and the inner circumferential surface of the chamber as a polygonal shape such as an ellipse, square or triangle.

In addition, while in the embodiment described above the cylinder 26 is affixed to the confluent branch part 12 by provision of the slit 16a in the rubber stopper 16 and inserting of the male luer part 26b in the slit 16a, replacing the cylinder 26, a connector insert part or a needle such as an injection needle or a blunt needle can be inserted into the rubber stopper 16. Notably, when an injection needle is inserted, the need for provision of a slit 16a in the rubber stopper 16 is eliminated. In addition, while in the embodiment described above the confluent branch part 12 is configured from a confluent branch tube main body 12a, a cover 17 and a rubber stopper 16, the confluent branch part may be configured from a confluent branch tube main body and rubber stopper in which the rubber stopper is affixed to the confluent branch tube main body. Furthermore, the shape and materials of the other sections from which the liquid coinjector is configured may be altered as appropriate.

As can be seen from the above description, the configuration of the liquid coinjector pertaining to at least one embodiment of this present invention is characterized by comprising a liquid coinjector main body comprising a cylindrically-formed chamber, a pair of main branch tubes that extend outward from both sides of an outer circumferential surface of the chamber and comprise flow passages that communicate with the interior of the chamber, and a confluent branch part extending outward from the outer circumferential surface of the chamber at a predetermined angle with respect to the pair of main branch tubes that comprises a flow passage that can communicate with or be cut off from the interior of the chamber; and a valve body arranged in the chamber to be movable in the axial direction of the chamber in a state in which an end part thereof protrudes from at least one of two side opening parts of the chamber which, as a result of being moved by the protruding end part being pushed into the chamber, affords cutoff of one of the pair of main branch tubes from the chamber and communication between the pair of main branch tubes and the chamber by way of the confluent branch part.

The liquid coinjector of the configuration described above comprises a valve body that is movable along the axial direction of a chamber in a state in which an end part thereof protrudes from an opening of the chamber. By a reciprocating motion of the valve body in the chamber as a result of the end part of the valve body protruding from the chamber being pushed into the chamber, the valve body affords cutoff of one of the pair of main branch tubes from the chamber and communication of the pair of main branch tubes with the confluent branch part by way of a section on the chamber side. In addition, the confluent branch part comprises a flow passage able to communicate with and be cut off from the interior of the chamber.

Accordingly, the pair of main branch tubes can communicate with the confluent branch part by way of a section on the chamber side as a result of movement of the valve body in the chamber whereupon, as a result of communication of the flow passage of the confluent branch part with the chamber, communication between the outer-side end parts of each of the three branch tubes is possible. By virtue of this, two types of liquid medicine can be supplied to the body of a patient. In addition, communication with the pair of main branch tubes alone is possible by cutoff of the flow passage of the confluent branch part from the chamber in this state. Furthermore, communication between one of the pair of main branch tubes with the confluent branch part is possible by cutoff of the other of the pair of main branch tubes from the chamber in the state in which the confluent branch part flow passage is in communication with the chamber.

According to this liquid coinjector, because the switching operation between communication and cutoff of the pair of main branch tubes requires simply that the end part of the valve body protruding from the chamber be pushed into the interior of the chamber, the position of the valve body is simply and easily ascertained and, accordingly, the risk of operation error is unlikely. In addition, because the operation for switching the flow passage requires only that the valve body be moved in the axial direction of the chamber, an operating part and so on for moving the valve body is unnecessary and, accordingly, the obstruction caused by an operating part and so on protruding from the outer circumferential surface of the chamber is removed.

Furthermore, because a state in which the axial direction of the chamber lies in the horizontal direction is established when a liquid coinjector such as this is located, for example, above the bed of the patient, contact with the body of the patient resulting in change in the position of the valve body is unlikely to occur. Moreover, provided it is tubular and extends in the axial direction, a chamber of any shape, for example, a cylinder, square cylinder, triangular cylinder, elliptical cylinder or a semi-circular cylinder shape, may be used. In addition, a valve body formed by cutting away of part of a columnar body for the purpose of closing just one of a pair of branch tubes and in which a flow passage configured as a hole formed in the interior of the columnar body can be used as the valve body.

In addition, the liquid coinjector pertaining to at least one embodiment of the present invention is further characterized by provision in an outer circumferential surface of the valve body of a first groove part by which one main branch tube of the pair of main branch tubes and the confluent branch part communicate and a second groove part by which the other main branch tube of the pair of main branch tubes and the confluent branch part communicate when the valve body is positioned in one side of the chamber, and provision of a cutoff surface by which one main branch tube of the pair of main branch tubes is cut off from the confluent branch part when the valve body is positioned in the other side of the chamber. By virtue of this, the valve body constitutes a simple structure that enables reliable switching between the flow passages to be performed.

The liquid coinjector pertaining to at least one embodiment of the present invention is further characterized by provision of a guide part extending in an axial direction in a section of the chamber in which the valve body is arranged, and provision in the valve body of a guided part that is movable with respect to the guide part in an engaged state with the guide part, the valve body being able to move in the axial direction only of the chamber.

Because, by virtue of this, rotation of the valve body in the chamber in the direction around the axis of the chamber can be prevented, the valve body can be moved along a precise trajectory. For this reason, imprecise switching of the flow passages as a result of displacement of the position of the valve body with respect to the chamber does not occur. Moreover, the guide part and the guided part of this case are configured from a groove part and a ridge, and the shape of the inner circumferential surface of the chamber and the outer circumferential surface of the valve body can be configured in a shape that prevents rotation of the valve body with respect to the chamber by formation in, for example, a polygonal shape such as an ellipse, a square or a triangle.

The liquid coinjector pertaining to at least one embodiment of the present invention is further characterized by provision of an engage part extending in a circumferential direction in a section of the chamber in which the valve body is arranged, and provision in the valve body of an engaged part that is detachable from the engage part, the valve body being able to be maintained in a stationary state at a predetermined position of the chamber by engagement of the engage part with the engaged part.

The "detachable" of this case describes the relationship whereby, while the valve is able to be moved in a state in which the engage part and engaged part are engaged when the end part protruding from the chamber is pushed into the chamber at a predetermined force, the engage part and the engaged part will not disengage and, accordingly, the state in which the valve body is fixed to this position will be maintained, if the force at which the end part of the valve body protruding from the chamber is less than this predetermined force. That is to say, the liquid coinjector pertaining to the present invention is configured so that the valve body is moved only when an operator moves the valve body by a deliberate application of force. Proper operation of the valve body is possible as a result.

The liquid coinjector pertaining to at least one embodiment of the present invention is further characterized in that the confluent branch part is configured from a substantially cylinder-shaped confluent branch tube and a rubber stopper affixed to an interior upper-end side of the confluent branch tube, communication between the chamber and a tubular member being made possible by passing of the tubular insert member through the rubber stopper. By virtue of this, the flow passage of the confluent part can communicate with and be cut off from the chamber by a simple method. In addition, the confluent branch tube of this case can be configured either from a tubular part that extends from the outer circumferential surface of the chamber, or by the further assembly in a tubular part that extends from the outer circumferential surface of the chamber of a substantially cylinder-shaped linking member. Furthermore, a connector insert part, a male luer part for a connector or cylinder, or a needle such as an injection needle or a blunt needle or the like can be employed as the tubular insert member. In addition, for cases in which the tip-end part of the tubular insert member is not formed in a pointed shape, a slit through which the tubular insert member is able to pass can be provided in the rubber stopper.

Having described the invention in detail, it will be apparent that modifications and variations are possible without departing from the scope of the invention defined in the appended claims.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above constructions, products, and methods without departing from the scope of the invention, it is intended that all matter contained in the above description and shown in the accompanying drawings shall be interpreted as illustrative and not in a limiting sense.

What is claimed is:

1. A liquid coinjector comprising:
   a main body defining a chamber having an axis perpendicular to the first and second connection ports, the first and second connection ports extending outwardly from said chamber and a third connection port extending outwardly from said chamber at a predetermined angle with respect to said first and second connection ports; and
   a valve body arranged in said chamber and movable within said chamber in a direction parallel to said axis between a first position in which both said second and third connection ports are in fluid flow communication with said first connection port and a second position in which only said third connection port is in fluid flow connection with said first connection port, characterized by said valve body defines a first groove part and a second groove part, the first groove part being shaped so as to provide said fluid flow communication between said first connection port and said second and third communication ports when said valve body is in said first position and said second groove part being shaped so as to provide said fluid flow communication between said first connection port and said third communication port when said valve body is in said second position and wherein said valve body includes an isolating surface region by fluid flow connection from said second connection port is cut off when said valve body is in said second position.

2. The liquid coinjector according to claim 1, wherein the second groove part is substantially L-shaped.

3. The liquid coinjector according to claim 1 wherein said main body chamber is arranged to define a guide part extending in an axial direction and said valve body comprises a guided part that is arranged to engage with said guide part to guide the movement of said valve body within the chamber is said axial direction.

4. The liquid coinjector according to claim 1 or claim 3, wherein said main body chamber is arranged to define an engaging part extending in a circumferential direction and said valve body comprises an engaged part that is releasably engageable with said engaging part, said valve body being maintainable in a stationary state at a predetermined position within said chamber by engagement of said engaging part with said engaged part.

5. The liquid coinjector according to claim 1 wherein said third connection port includes a rubber seal arranged within an interior surface of said third connection port.

6. The liquid coinjector according to claim 1 wherein said valve body extends outwardly from said chamber in either of said first and second positions.

7. The liquid coinjector according to claim 1,
   wherein the second groove part is substantially L-shaped, and
   wherein said main body chamber is arranged to define a guide part extending in an axial direction and said valve body comprises a guided part that is arranged to engage with said guide part to guide the movement of said valve body within the chamber in said axial direction.

* * * * *